(12) United States Patent
Gerits

(10) Patent No.: US 7,449,141 B2
(45) Date of Patent: Nov. 11, 2008

(54) IMMERSION MEASURING PROBE, PARTICULARLY A DROP-IN-MEASURING PROBE

(75) Inventor: Erik Gerits, Genk (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 11/412,020

(22) Filed: Apr. 26, 2006

(65) Prior Publication Data

US 2006/0236750 A1 Oct. 26, 2006

(30) Foreign Application Priority Data

Apr. 26, 2005 (DE) .................. 10 2005 019 665

(51) Int. Cl.
*G01N 27/26* (2006.01)
(52) U.S. Cl. ................. 266/99; 266/78; 266/88
(58) Field of Classification Search ............ 266/78, 266/88, 96, 99
See application file for complete search history.

(56) References Cited

U.S. PATENT DOCUMENTS

| 4,906,349 A | 3/1990 | Beatrice et al. |
| 4,964,736 A * | 10/1990 | Cure et al. ............... 374/140 |
| 5,584,578 A * | 12/1996 | Clauss, Jr. ............... 374/140 |
| 5,656,143 A | 8/1997 | Swetnam et al. |
| 6,299,348 B1 * | 10/2001 | Theuwis ............... 266/88 |
| 2004/0084328 A1 | 5/2004 | Jones et al. |
| 2004/0173473 A1 | 9/2004 | Habets |

FOREIGN PATENT DOCUMENTS

| DE | 3021 949 C2 | 9/1982 |
| DE | 195 31 661 A1 | 10/1996 |
| DE | 196 52 596 A1 | 7/1998 |
| DE | 198 49 433 C1 | 4/2000 |
| DE | 101 03 701 C1 | 9/2002 |
| DE | 102 03 121 A1 | 8/2003 |
| EP | 0 363 616 A2 | 4/1990 |
| WO | 0206804 A2 | 1/2002 |

OTHER PUBLICATIONS

European Search Report dated Aug. 2, 2006.

\* cited by examiner

*Primary Examiner*—Scott Kastler
(74) *Attorney, Agent, or Firm*—Panitch Schwarze Belisario & Nadel LLP

(57) ABSTRACT

An immersion measuring probe, particularly a drop-in measuring probe for metal melts, is provided having a measuring head, on which at least one sensor carrier having at least one sensor is arranged. The sensor carrier is held at or in an opening in the measuring head. At least a part of the measuring head is in electrical contact with a counter electrode of an electrochemical sensor arranged on the measuring head and forming a bath contact for the electrochemical sensor.

8 Claims, 2 Drawing Sheets

IMMERSION MEASURING PROBE, PARTICULARLY A DROP-IN-MEASURING PROBE

BACKGROUND OF THE INVENTION

The invention relates to an immersion measuring probe, particularly a drop-in measuring probe for metal melts. The probe has a measuring head on which at least one sensor carrier with at least one sensor is arranged, and the sensor carrier is held at or in an opening of the measuring head.

Measuring probes of this type are known, for example, from German Patent DE 198 49 433 C1. Drop-in measuring probes are thrown from a certain height from a holder into a molten metal. The measuring head mounted at one end of a carrier tube is generally made of steel in order to provide the mass required to penetrate the slag layer built up on molten steel or iron. Inside the carrier tube a signal cable is wound up, which is connected with a measurement system and which unwinds from the carrier tube during the fall into the molten metal. In the measuring head a sensor carrier having at least one sensor is arranged, for example a temperature sensor or an electrochemical element for measurement of the oxygen content of the molten metal. When penetrating the slag layer lying on top of the molten steel, slag may adhere to the measuring head. This slag adhering to the measuring head, and perhaps to the protective cap of the sensors, can influence the measurement of the properties of the molten steel and lead to measurement errors.

Besides the contact of their solid electrolyte material with the molten metal, electrochemical sensors also need a so-called bath contact between their so-called counter electrode and the molten metal. The bath contact is often achieved outside the measuring probe via signal lines to the molten metal (See German Patent DE 30 21 949 C2), or, as described for example in German published patent application Nos. DE 195 31 661 A1 or DE 196 52 596 A1, as an additional component which itself must be correspondingly protected. These publications, however, do not relate to drop-in measuring probes and are not suitable for the particular mechanical loads (particularly shock loads) of such probes.

A sensor unit is known from German published patent application No. DE 102 03 121 A1, in which a sensor carrier is located at a measuring head, wherein the sensor carrier has a sensor and wherein the measuring head is in electrical contact with parts of the sensor. A similar sensor is known from European published patent application EP 363 616 A2. Further, a solid electrolyte tube is known from German Patent DE 101 03 701 C1, which is used in a measurement system for the determination of oxygen in molten metals. The solid electrolyte tube is closed on its backside end with a locking cap.

BRIEF SUMMARY OF THE INVENTION

The invention is based on the object of providing a simply constructed and reliably functioning immersion measuring probe, particularly a drop-in measuring probe.

The object is achieved by an immersion measuring probe, particularly a drop-in measuring probe, for metal melts, having a measuring head, on which at least one sensor carrier with at least one sensor is arranged. The sensor carrier is held at or in an opening in the measuring head, and at least a part of the measuring head is in electrical contact with a counter electrode of an electrochemical sensor arranged at the measuring head and forms a bath contact with the electrochemical sensor. The probe is characterized by a first locking element arranged on the sensor carrier which engages with a second locking element arranged on the measuring head.

Since at least a part of the measuring head is in electrical contact with a counter electrode of an electrochemical sensor arranged on the measuring head and forms a bath contact for the electrochemical sensor, a reliable bath contact thereby results from simple, short contact paths and a large bath contact surface. The arrangement is very stable and can withstand the mechanical loads during drop-in of the probe into molten steel. The measuring head is preferably made of metal. In particular, it is expedient for the sensor carrier to have a locking connection with the measuring head, in order to ensure a simple installation. On the sensor carrier, preferably on its end arranged within the measuring head, a first locking element is arranged which engages with a second locking element located on the measuring head. It is furthermore advantageous for a contact element to be arranged on the sensor carrier, preferably on its end arranged within the measuring head, which electrically connects the counter electrode with the measuring head. It is expedient for the first locking element to be located on this contact element.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
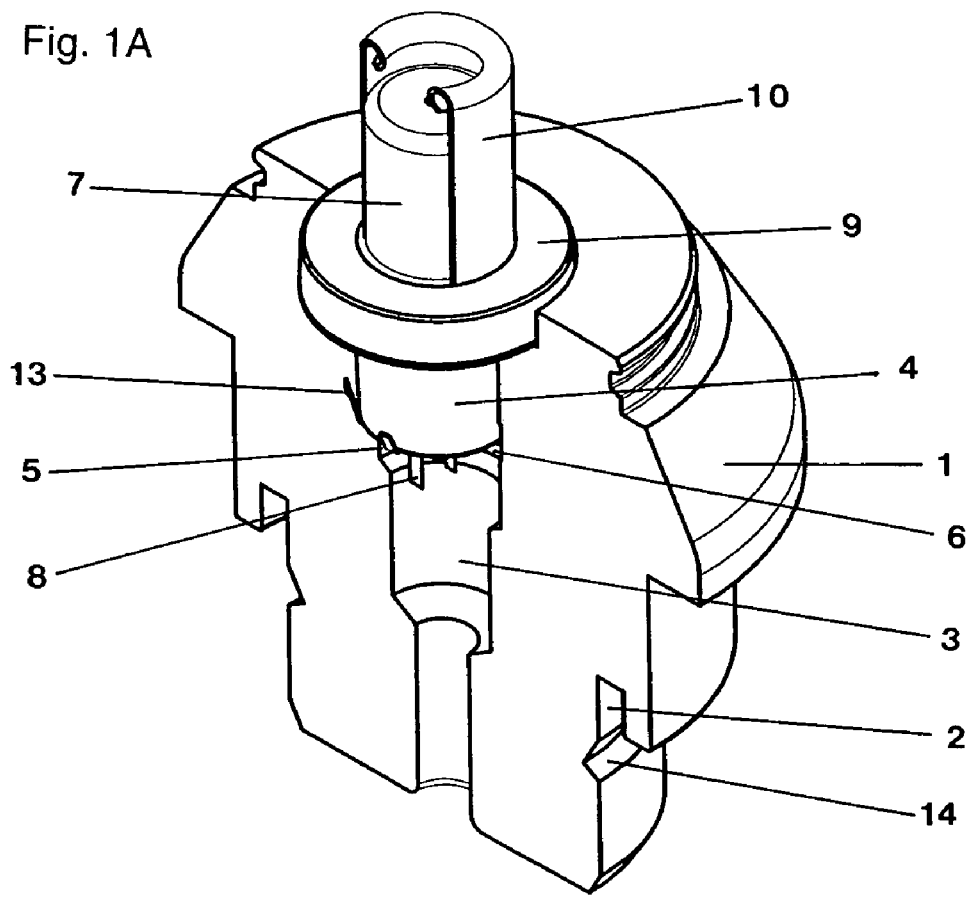
FIG. 1A is a broken away, top perspective section of one embodiment of the measuring head of the invention.
Figure 1B:
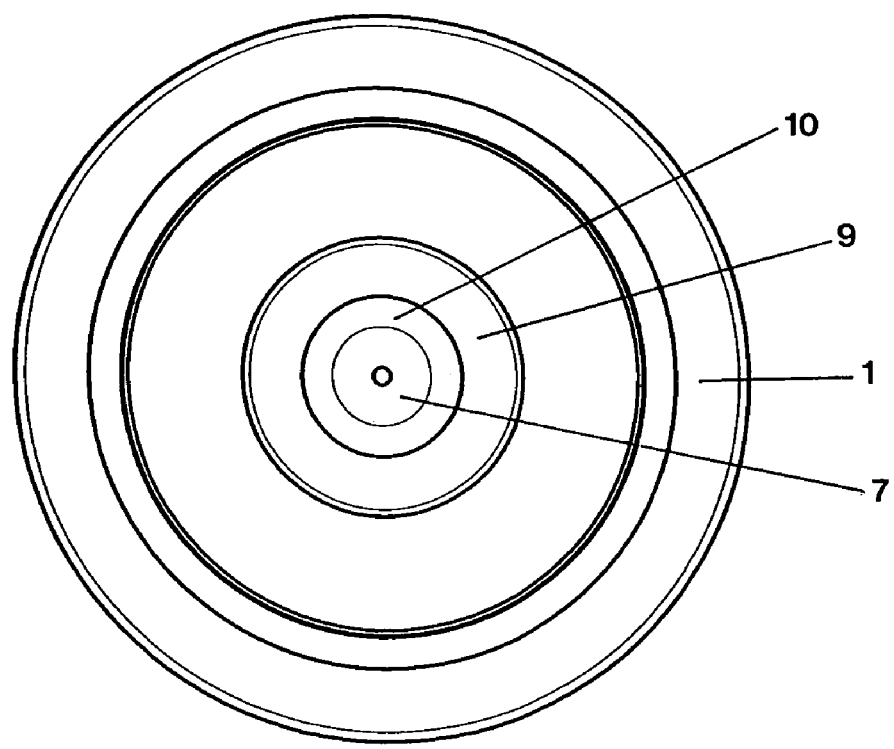
FIG. 1B is a plan view of the measuring head of FIG. 1.

FIGS. 1A and 1B show measuring head 1 of a drop-in measuring probe. Measuring head 1 is usually mounted on one end of a carrier tube, which can be made of cardboard. Ring groove 2 or ring groove 14 of measuring head 1 can be used for this purpose. The carrier tube is not shown in the drawing for reasons of clarity.

Measuring head 1 is made of steel. It has a central longitudinal bore 3. In the immersion end of measuring head 1, a sensor carrier 4 is mounted in bore 3. Sensor carrier 4 has, on its rear end facing away from the immersion end, one or more hooks 5 as a first locking element, which engage in an annular groove 6 as a second locking element, when the sensor carrier 4 is inserted into bore 3, and which fix sensor carrier 4 in bore 3. Sensor head 4 has one or more sensors under a protective cap 7, for example a thermo-element and/or an electrochemical sensor for determination of the gas content of the molten steel for whose analysis the immersion measuring probe is used. The sensor is connected via contacts 8 on the rear end of sensor carrier 4 to signal lines, which are connected through the bore 3 to a measurement unit or a computer.

Sensor carrier 4 arranged in bore 3 of measuring head 1 has a ring 9 made of casting sand. It is also possible to form the entire sensor carrier 4 of casting sand. At least ring 9 can also be made of cardboard or a similar combustible or gas-containing porous material. The sensor of the sensor carrier is covered by a protective cap 7, which in turn is covered with a cardboard cap 10. Both cardboard cap 10 and protective cap 7 are destroyed upon entry into the molten steel, so that the sensor comes into contact with the molten steel. While penetrating the slag layer lying on top of the molten steel or when immersed in the molten steel, the measuring head is quickly heated to the temperature of the molten steel. The gas present in the pores of the casting sand thereby experiences a rapid increase in volume, so that it emerges very quickly from ring 9, and thereby actually rips away any slag adhering to sensor carrier 4 or protective cap 7. Consequently, the slag does not influence the immediate vicinity of the sensor, so that the measurement accuracy is increased.

Sensor carrier 4 can also be made of steel. Measuring head 1 can in principle also be used without a carrier tube.

Figure 2:
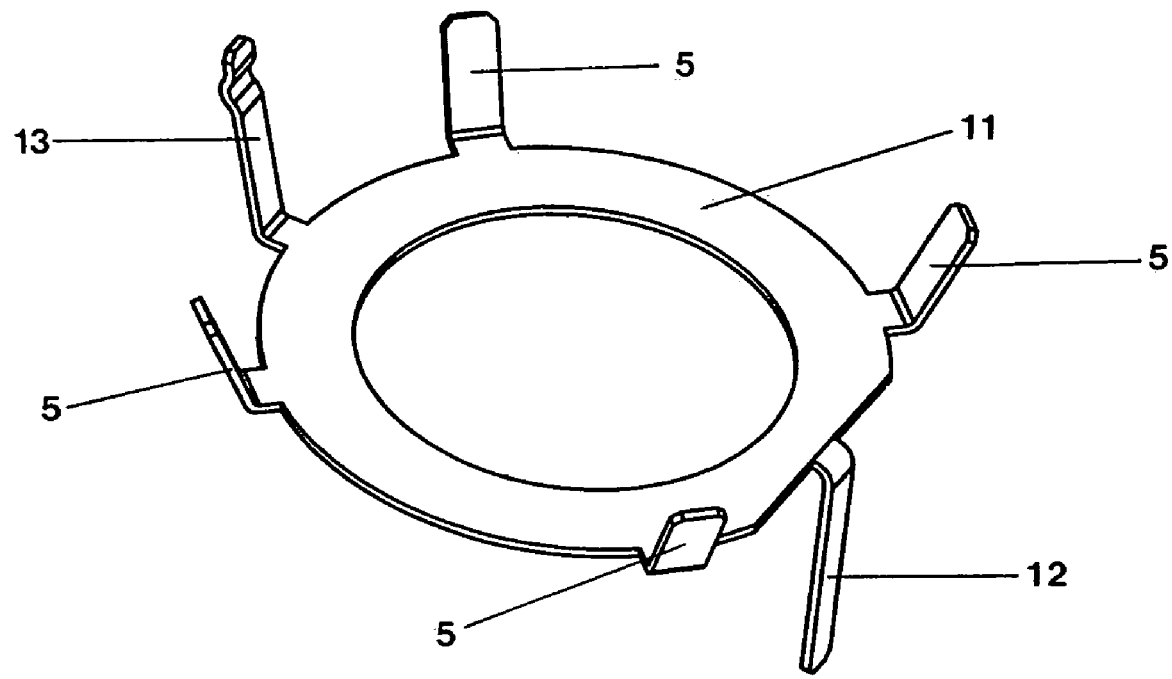
FIG. 2 is a top perspective view of a contact element of the invention.

An electrochemical element arranged on sensor carrier 4 needs a so-called bath contact for its functioning. This bath contact is expediently produced by the corresponding contact of the electrochemical element leading from the underside of sensor carrier 4 (the counter electrode) being directly connected electrically via a contact element 11 (shown in FIG. 2) to the metallic measuring head 1, so that the body of the measuring head 1 itself makes the electrical contact with the molten metal. Contact element 11 is essentially formed as a metal ring and is arranged on the front end of sensor carrier 4 in the interior of measuring head 1. A contact strip 12 serves for contact with the counter electrode and another contact strip 13 serves for contact with measuring head 1. This enables, on the one hand, simple mounting of the sensor carrier 4 in measuring head 1, since both must merely be inserted into one another and then the locking connection is engaged. On the other hand, a reliable bath contact results from simple, short contact paths and a large bath contact surface. The arrangement is very stable and can withstand the mechanical load upon drop-in of the probe into molten steel.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A drop-in immersion measuring probe for being thrown from a certain height from a holder into metal melts, the probe comprising a measuring head having a mass sufficient to penetrate a slag layer built up on the metal melts, on which at least one sensor carrier with at least one sensor is arranged, the sensor carrier being held at or in an opening in the measuring head, at least a part of the measuring head being in electrical contact with a counter electrode of an electrochemical sensor arranged at the measuring head and forming a bath contact with the electrochemical sensor, and a first locking element arranged on the sensor carrier, the first locking element engaging with a second locking element arranged on the measuring head, wherein the first and second locking elements comprise a hook engaging in an annular groove.

2. The drop-in immersion measuring probe according to claim 1, wherein the measuring head is made of metal.

3. The drop-in immersion measuring probe according to claim 1, wherein the sensor carrier is in locking connection with the measuring head.

4. The drop-in immersion measuring probe according to claim 1, wherein the first locking element is arranged on an end of the sensor carrier located in the interior of the measuring head.

5. The drop-in immersion measuring probe according to claim 1, wherein a contact element is arranged on the sensor element and makes an electrically conducting connection of the counter electrode with the measuring head.

6. The drop-in immersion measuring probe according to claim 5, wherein the contact element is arranged on an end of the sensor element located in an interior of the measuring head.

7. The drop in immersion measuring probe according to claim 5, wherein the first locking element is arranged on the contact element.

8. The drop-in immersion measuring probe according to claim 1, wherein the first locking element comprises at least two hooks.

* * * * *